United States Patent [19]

Hamprecht et al.

[11] Patent Number: 4,472,191

[45] Date of Patent: Sep. 18, 1984

[54] 1,2,4,6-THIATRIAZINE-1,1-DIOXIDES AND THEIR USE FOR CONTROLLING UNDESIRABLE PLANT GROWTH

[75] Inventors: Gerhard Hamprecht, Weinheim; Rolf-Dieter Acker, Leimen; Hubert Sauter, Mannheim; Hans Theobald, Limburgerhof; Bruno Wuerzer, Otterstadt, all of Fed. Rep. of Germany

[73] Assignee: BASF Aktiengesellschaft, Fed. Rep. of Germany

[21] Appl. No.: 436,034

[22] Filed: Oct. 22, 1982

[30] Foreign Application Priority Data

Nov. 2, 1981 [DE] Fed. Rep. of Germany ....... 3143381

[51] Int. Cl.$^3$ .................... C07D 285/00; A01N 43/72
[52] U.S. Cl. ............................ 71/91; 544/7
[58] Field of Search ................. 544/7; 71/91

[56] References Cited

U.S. PATENT DOCUMENTS

| 4,013,447 | 3/1977 | Kay ........................ 544/7 |
| 4,316,014 | 2/1982 | Hamprecht ............... 544/7 |
| 4,316,015 | 2/1982 | Hamprecht et al. ...... 544/7 |
| 4,343,648 | 8/1982 | Hamprecht et al. ...... 544/7 |

FOREIGN PATENT DOCUMENTS 0029908  6/1981  European Pat. Off. .

OTHER PUBLICATIONS

C.A., (1980), 92, 76465a, Karady et al.

Primary Examiner—John M. Ford
Attorney, Agent, or Firm—Keil & Weinkauf

[57] ABSTRACT

1,2,4,6-Thiatriazine-1,1-dioxides of the formula

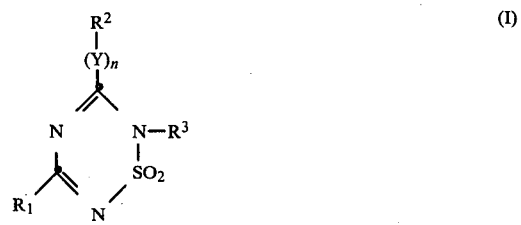

(I)

where $R^1$, $R^2$, $R^3$, Y and n have the meanings given in the description, are used for controlling undesirable plant growth.

11 Claims, No Drawings

1,2,4,6-THIATRIAZINE-1,1-DIOXIDES AND THEIR USE FOR CONTROLLING UNDESIRABLE PLANT GROWTH

The present invention relates to 1,2,4,6-thiatriazine-1,1-dioxides, herbicides containing these compounds as active ingredients, and their use for controlling undesirable plant growth.

It has been disclosed that 6H-1,2,4,6-thiatriazin-5-one-1,1-dioxide derivatives have a herbicidal action (German Laid-Open Applications DOS No. 2,508,832 and DOS No. 2,933,889).

We have found that 1,2,4,6-thiatriazine-1,1-dioxides of the formula

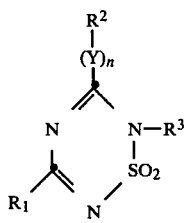

where $R^1$ is hydrogen or a saturated or unsaturated, straight-chain or branched aliphatic radical of no more than 10 carbon atoms, or is a saturated, straight-chain or branched aliphatic radical of no more than 10 carbon atoms which is substituted by halogen, alkoxy or alkylmercapto of 1 to 4 carbon atoms, or is an alkylamino or dialkylamino radical where alkyl is of 1 to 6 carbon atoms, cycloalkyl of 3 to 7 carbon atoms, or phenyl which is unsubstituted or substituted by halogen, alkyl or alkoxy of 1 to 4 carbon atoms, or is unsubstituted or halogen-substituted benzyl, or is $R^4$—X—, where $R^4$ has the meanings given for $R^1$, except alkylamino and dialkylamino, and X is oxygen, sulfur, —SO— or —SO$_2$—, $R^2$ is a saturated or unsaturated, straight-chain or branched aliphatic radical of no more than 10 carbon atoms which is substituted by cyano, thiocyano, nitro, alkenyloxy, alkynyloxy, alkenylmercapto or alkynylmercapto, each of no more than 4 carbon atoms, or by vinylketo, or is an alkyleneglycolalkyl, alkyleneglycolalkenyl or alkyleneglycolalkynyl radical of no more than 6 carbon atoms which is substituted by alkyl, alkenyl or alkynyl, each of no more than 4 carbon atoms, or is an alkenyl or alkynyl radical, each of no more than 4 carbon atoms, which is substituted by alkoxycarbonyl or alkylmercaptocarbonyl of no more than 5 carbon atoms, or is an alkylideneamino or dialkylmethylideneamino radical of no more than 6 carbon atoms, or a phenylalkyl, phenylalkenyl or phenylalkynyl radical of 8 to 12 carbon atoms which is unsubstituted or substituted in the phenyl ring by halogen, alkyl, haloalkyl, alkoxy, haloalkoxy, alkylmercapto or haloalkylmercapto, each of no more than 4 carbon atoms, nitro, cyano or thiocyano, $R^3$ is hydrogen or a saturated or unsaturated, straight-chain or branched aliphatic radical of no more than 10 carbon atoms, or is a saturated, straight-chain or branched aliphatic radical of no more than 10 carbon atoms which is substituted by halogen or alkoxy of 1 to 4 carbon atoms, or is cycloalkyl of 3 to 7 carbon atoms, Y is oxygen, sulfur, —SO— or —SO$_2$— and n is 1, or where $R^2$ is benzyl which is substituted by nitro or by halogen and nitro, or is a phenoxyalkyl, phenoxyalkenyl or phenoxyalkynyl radical of 8 to 12 carbon atoms which is substituted in the phenyl ring by halogen, alkyl, haloalkyl, alkoxy, haloalkoxy, alkylmercapto or haloalkylmercapto, each of no more than 4 carbon atoms, nitro, cyano or thiocyano, when $R^1$ is $R^4$—X— and n is 1, or where $R^2$ is dialkylphosphono when n is 0, have a good herbicidal action.

In formula I, $R^1$ and $R^3$ are each hydrogen or a saturated or unsaturated, straight-chain or branched aliphatic radical of no more than 10 carbon atoms, for example alkyl of no more than 10, preferably no more than 4, carbon atoms, or an alkenyl or alkynyl radical of no more than 10, preferably no more than 4, carbon atoms, eg. methyl, ethyl, n-propyl, isopropyl, n-butyl, isobutyl, sec.-butyl, tert.-butyl, n-pentyl, tert.-amyl, n-hexyl, pent-3-yl, 1,2-dimethyl-n-propyl, 1,3-dimethyl-n-butyl, 1-ethyl-2-methyl-n-propyl, 1,2,2-trimethyl-n-propyl, 1,2-dimethyl-4-hexyl, allyl, methallyl, crotyl, 2-ethylhex-2-enyl, hex-5-enyl, 2-methylbut-2-enyl, 2-methylbut-3-enyl, but-1-en-3-yl, 2-methylbut-1-en-4-yl, 2-methylbut-2-en-4-yl, 3-methylbut-1-en-3-yl, propargyl, but-1-yn-3-yl or but-2-ynyl, or are each a saturated, straight-chain or branched aliphatic radical of no more than 10, preferably no more than 4, carbon atoms which are substituted by halogen or alkoxy of 1 to 4 carbon atoms, for example haloalkyl of no more than 10, preferably 1 to 4, carbon atoms, or alkyl of no more than 10, preferably no more than 4, carbon atoms which are substituted by alkoxy of 1 to 4 carbon atoms, eg. 2-chloroethyl, 2-chloro-n-propyl, 3-chloro-n-propyl, 2-chloro-sec.-butyl, 2-chloro-isobutyl, 2-fluoro-sec.-butyl, 2-fluoroisobutyl, 2-fluoroisopropyl, chloro-tert.-butyl, 2,2,2-trifluoroethyl, 2-methoxyethyl, 2-ethoxyethyl, 3-methoxy-n-propyl, 2-methoxyisopropyl, 3-methoxy-n-butyl, 1-methoxy-sec.-butyl, methoxy-tert.-butyl, ethoxy-tert.-butyl, 2-methoxy-n-butyl and 4-methoxy-n-butyl, or are each cycloalkyl of 3 to 7 carbon atoms, eg. cyclopropyl, cyclopentyl or cyclohexyl.

$R^1$ is furthermore an alkylamino or dialkylamino radical where alkyl is of 1 to 6, preferably 1 to 4, carbon atoms, eg. methylamino, dimethylamino, ethylamino, isopropylamino, n-butylamino, methylethylamino or diisopropylamino, or is a saturated, straight-chain or branched aliphatic radical of no more than 10 carbon atoms which is substituted by alkylmercapto of 1 to 4 carbon atoms, for example alkyl of not more than 10, preferably 1 to 4, carbon atoms which is substituted by alkylmercapto of 1 to 4 carbon atoms, eg. 2-methylmercaptoethyl, 2-ethylmercaptoethyl, 3-methylmercapto-n-propyl, 3-methylmercapto-n-butyl, 1-methylmercapto-sec.-butyl, methylmercapto-tert.-butyl or 2-methylmercapto-butyl, or is phenyl which is unsubstituted or substituted by halogen, alkyl or alkoxy of 1 to 4 carbon atoms, or is benzyl which is unsubstituted or halogen-substituted in the phenyl ring, eg. phenyl, 4-chlorophenyl, 3,4-dichlorophenyl, o-, m- and p-tert.-butylphenyl, o-, m- and p-methoxyphenyl, o-, m- and p-methylphenyl, 4-methoxy-3-chlorophenyl, 2-methyl-4-chlorophenyl, benzyl, 2,6-dichlorobenzyl, 2-chloro-6-fluorobenzyl, 2,6-difluorobenzyl and o-, m- and p-chlorobenzyl.

$R^1$ can furthermore be $R^4$—X—, where $R^4$ has the meanings given for $R^1$, except alkylamino and dialkylamino, and X is oxygen, sulfur, —SO— or —SO$_2$—, preferably oxygen or sulfur.

In formula I, $R^2$ is a saturated or unsaturated, straight-chain or branched aliphatic radical of no more than 10, preferably no more than 4, carbon atoms which is substituted by cyano, thiocyano, nitro, alkenyloxy, alkynyloxy, alkenylmercapto or alkynylmercapto, each having no more than 4 carbon atoms, or by vinylketo, eg. 2-cyanoethyl, 2-cyano-n-propyl, 3-cyano-n-propyl, 4-cyano-n-butyl, 3-cyanoprop-2-enyl, 4-cyanobut-2-ynyl, 2-nitroethyl, 2-nitro-n-propyl, 3-nitro-n-propyl, 3-nitroprop-2-enyl-2-allyloxyethyl, 2-proparglyoxyethyl, 2-allyloxy-n-propyl, 2-propargyloxy-n-propyl, 3-allyloxy-n-propyl, 4-allyloxy-but-2-ynyl, 2-allylmercaptoethyl, 2-propargylmercaptoethyl, 2-allylmercapto-n-propyl, vinylketoethyl, 2-thiocyanoethyl, 2-thiocyano-n-propyl, 3-thiocyano-n-propyl, 4-thiocyano-n-butyl or 4-thiocyanobut-2-ynyl or is alkyleneglycolalkyl of no more than 6, preferably no more than 4, carbon atoms which is substituted by alkyl, alkenyl, or alkynyl, each of no more than 4 carbon atoms, eg. 2-(methoxyglycol)-ethyl, 2-(allyloxyglycol)-ethyl, 2-(propargyloxyglycol)-ethyl, 3-(methoxyglycol)-n-propyl or 4-(methoxyglycol)-n-butyl, or is alkenyl or alkynyl, each of no more than 4 carbon atoms, which is substituted by alkoxycarbonyl or alkylmercaptocarbonyl, each of no more than 5 carbon atoms, eg. 3-methoxycarbonylprop-2-enyl, 3-ethoxycarbonylprop-2-enyl, 3-n-propoxycarbonylprop-2-enyl, 3-n-butoxycarbonylprop-2-enyl, 3-methoxycarbonylprop-2-ynyl, 3-ethoxycarbonylprop-2-ynyl, 3-n-butoxycarbonylprop-2-ynyl or 3-methylmercaptocarbonylprop-2-enyl, or is an alkylideneamino or dialkylmethylideneamino radical of no more than 6 carbon atoms, eg. ethylideneamino, n-propylideneamino, n-butylideneamino, prop-2-ylideneamino, but-2-ylideneamino, pent-2-ylideneamino, pent-3-ylideneamino or hex-3-ylideneamino, or is a phenylalkyl, phenylalkenyl or phenylalkynyl radical of 8 to 12 carbon atoms which is unsubstituted or substituted in the phenyl ring by halogen, alkyl, haloalkyl, alkoxy, haloalkoxy, alkylmercapto or haloalkylmercapto, each of no more than 4 carbon atoms, cyano, nitro or thiocyano, eg. 2-(o-, m- or p-chlorophenyl)-ethyl, 2-(2',4'-dichlorophenyl)-ethyl, 2-(2',4',6'-trichlorophenyl)-ethyl, 2-(3',5'-dichlorophenyl)-ethyl, 2-(o-, m- or p-tolyl)-ethyl, 2-(3',4'-xylol)-ethyl, 2-(o-, m- or p-trifluoromethylphenyl)-ethyl, 2-(o-, m- or p-anisyl)-ethyl, 2-(o-, m- or p-difluoromethoxyphenyl)-ethyl, 2-(o-, m- or p-chlorodifluoromethoxyphenyl)-ethyl, 2-(o-, m- or p-methylmercaptophenyl)-ethyl, 2-(o-, m- or p-trifluoromethylmercaptophenyl)-ethyl, 2-(o-, m- or p-cyanophenyl)-ethyl, 2-(o-, m- or p-thiocyanatophenyl)-ethyl, 3-(o-, m- or p-chlorophenyl)-n-propyl, 3-(o-, m- or p-trifluoromethylphenyl)-n-propyl, 2-phenylethyl, 3-phenyl-n-propyl, 4-phenyl-n-butyl, 5-phenyl-n-pentyl, 2-(o-, m- or p-nitrophenyl)-ethyl, 2-(3'-chloro-4'-methoxyphenyl)-ethyl, 2-(4'-chloro-3'-methoxyphenyl)-ethyl, 2-(2'-chloro-4'-trifluoromethylphenyl)-ethyl, 2-phenylethylene, 2-(o-, m- or p-chlorophenyl)-ethylene, 2-(o-, m- or p-tolyl)-ethylene, 2-(o-, m- or p-nitrophenyl)-ethylene, 3-phenylprop-2-enyl, 3-(o-, m- or p-chlorophenyl)-prop-2-enyl, 3-(o-, m- or p-tolyl)-prop-2-enyl or 3-(o-, m- or p-nitrophenyl)-prop-2-enyl, or, if n is 0, $R^2$ is a dialkylphosphono radical of the formula $(AlkO)_2P^O$—, where each alkyl is of 1 to 4 carbon atoms, eg. dimethylphosphono, methylethylphosphono or methyl-n-propylphosphono.

If $R_1$ is $R^4$—X—, $R^2$ may furthermore be benzyl which is substituted by nitro or by halogen and nitro, eg. o-, m- and p-nitrobenzyl, 2-chloro-6-nitrobenzyl, 4-chloro-6-nitrobenzyl or 4-nitro-6-chlorobenzyl, or may be a phenoxyalkyl, phenoxyalkenyl or phenoxyalkynyl radical of no more than 12, preferably no more than 10, carbon atoms which is substituted in the phenyl ring by halogen, alkyl, haloalkyl, alkoxy, haloalkoxy, alkylmercapto or haloalkylmercapto, each of no more than 4 carbon atoms, nitro, cyano or thiocyano, eg. 2-(o-, m- or p-chlorophenoxy)-ethyl, 2-(2',4'-dichlorophenoxy)-ethyl, 2-(2',4',6'-trichlorophenoxy)-ethyl, 2-(3',5'-dichlorophenoxy)-ethyl, 2-(3',4'-dichlorophenoxy)-ethyl, 2-(o-, m- or p-cresoxy)-ethyl, 2-(3',4'-dimethylphenoxy)-ethyl, 2-(o-, m- or p-trifluoromethylphenoxy)-ethyl, 2-(o-, m- or p-methoxyphenoxy)-ethyl, 2-(o-, m- or p-difluoromethoxyphenoxy)-ethyl, 2-(o-, m- or p-chlorodifluoromethoxyphenoxy)-ethyl, 2-(o-, m- or p-methylmercaptophenoxy)-ethyl, 2-(o-, m- or p-cyanophenoxy)-ethyl, 2-(o-, m- or p-thiocyanatophenoxy)-ethyl, 3-(o-, m- or p-chlorophenoxy)-n-propyl, 3-(o-, m- or p-trifluoromethylphenoxy)-n-propyl, 2-phenoxyethyl, 3-phenoxy-n-propyl, 4-phenoxy-n-butyl, 5-phenoxy-n-butyl, 2-(o-, m- or p-nitrophenoxy)-ethyl, 2-(3'-chloro-4'-methoxyphenoxy)-ethyl, 2-(2'-chloro-4'-trifluoromethylphenoxy)-ethyl, phenoxyethylene, 2-(o-, m- or p-chlorophenoxy)-ethylene, 2-(o-, m- or p-cresoxy)-ethylene, 2-(o-, m- or p-nitrophenoxy)-ethylene, 2-phenoxyprop-2-enyl, 3-(o-, m- or p-chlorophenoxy)-prop-2-enyl, 3-(o-, m- or o-cresoxy)-prop-2-enyl or 3-(o-, m- or p-nitrophenoxy)-prop-2-enyl.

Preferred compounds of the formula I are those in which $R^1$ is $R^4$—X—, where $R^4$ is alkyl of 1 to 4 carbon atoms, and X is oxygen, $R^2$ is dialkylphosphono where each alkyl is of 1 to 4 carbon atoms, $R^3$ is alkyl of 1 to 4 carbon atoms and n is 0, or those in which $R^1$ is $R^4$—X—, where $R^4$ is alkyl of 1 to 4 carbon atoms and X is oxygen or sulfur, $R^2$ is phenoxyalkyl of 7 to 10 carbon atoms which is substituted in the phenyl ring by halogen, cyano, nitro or alkyl, $R^3$ is alkyl of 1 to 4 carbon atoms and Y is oxygen or sulfur, or those in which $R^1$ and $R^3$ are each alkyl of 1 to 4 carbon atoms, $R^2$ is a cyano-substituted saturated or unsaturated aliphatic radical of no more than 4 carbon atoms, preferably alkyl, and Y is oxygen or sulfur, or those in which $R^1$ is $R^4$—X—, where $R^4$ is alkyl of 1 to 4 carbon atoms and X is oxygen or sulfur, $R^2$ is a cyano-substituted saturated or unsaturated aliphatic radical of no more than 4 carbon atoms, preferably alkyl, $R^3$ is alkyl of 1 to 4 carbon atoms and Y is oxygen or sulfur, or those in which $R^1$ and $R^3$ are each alkyl of 1 to 4 carbon atoms, $R^2$ is a phenylalkyl, phenylalkenyl or phenylalkynyl radical of 8 to 12 carbon atoms which is substituted in the phenyl ring by halogen, cyano, nitro or alkyl, preferably by halogen, and Y is oxygen or sulfur.

The 1,2,4,6-thiatriazine-1,1-dioxides of the formula I are obtained by a method wherein a compound of the formula

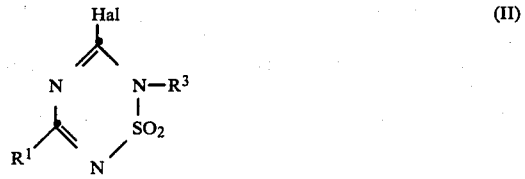

(II)

where $R^1$ and $R_3$ have the above meanings and Hal is halogen, is reacted with a compound of the formula

$H-(Y)_n-R^2$ (III)

where $R^2$, Y and n have the above meanings, or with an alkali metal salt, alkaline earth metal salt or ammonium salt of this compound, in the presence or absence of an inert organic solvent, and in the presence or absence of an acid acceptor, at from −50° to +150° C., under atmospheric or superatmospheric pressure, continuously or batchwise.

If 5-chloro-3-methyl-6-isopropyl-6H-1,2,4,6-thiatriazine-1,1-dioxide and β-hydroxypropionitrile are used as starting materials, the course of the reaction can be represented by the following equation:

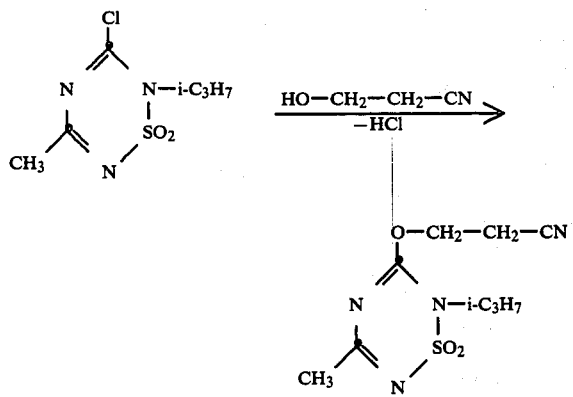

If 5-chloro-6-isopropyl-3-methoxy-6H-1,2,4,6-thiatriazine-1,1-dioxide and 2-(p-chlorophenyl)-ethanol are used as starting materials, the course of the reaction can be represented by the following equation:

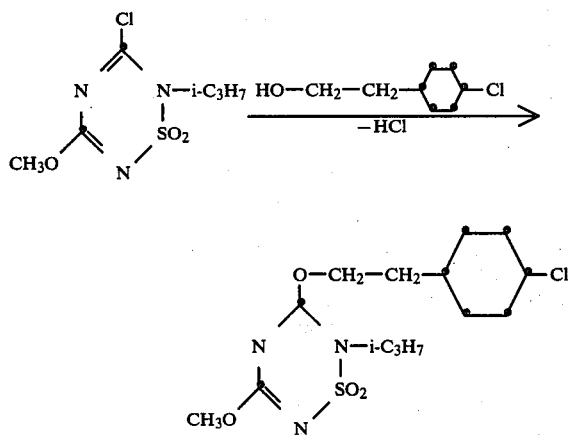

If 5-chloro-6-methyl-3-methylmercapto-6H-1,2,4,6-thiatriazine-1,1-dioxide and trimethyl phosphite are used as starting materials, the course of the reaction can be represented by the following equation:

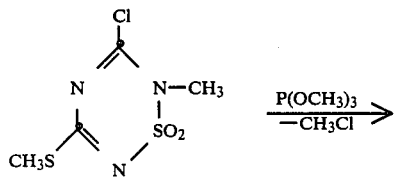

-continued

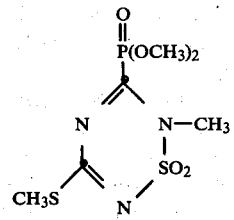

Advantageously, the reaction is carried out in a solvent or diluent which is inert under the particular reaction conditions. Examples of suitable solvents are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, m- and p-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β'-dichlorodiethyl ether; nitrohydrocarbons, eg. nitromethane, nitroethane, nitrobenzene, o-, m- and p-chloronitrobenzene and o-nitro-toluene; nitriles, eg. acetonitrile, butyronitrile, isobutyronitrile, benzonitrile and m-chlorobenzonitrile; aliphatic or cycloaliphatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; ketones, eg. acetone and methyl ethyl ketone; and, if appropriate, also water, and mixtures of the above. Advantageously, the solvent is used in an amount of from 100 to 2,000% by weight, preferably from 200 to 700% by weight, based on starting material II.

All conventional acid-binding agents can be used as the acid acceptors, preferred examples are tertiary amines, alkaline earth metal compounds, ammonium compounds, alkali metal compounds and mixtures of these. However, zinc compounds may also be used. Specific examples of basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

The acid acceptors are advantageously used in from 80 to 120% of the amount equivalent to the starting material II. However, the hydrogen halide formed can also be removed by sweeping with an inert gas, for example nitrogen.

The starting materials III required for the reaction are in general employed in from 80 to 120% of the amount equivalent to the starting material II. However, the starting material III may also be employed directly as the solvent. Alternatively, the starting material III can be initially introduced into one of the above diluents, after which the starting material II and an acid acceptor are added, simultaneously or in optional sequence, through two separate lines.

An advantageous method of preparing the novel compounds is to take the starting material II, in the presence or absence of one of the above diluents, and then to add the starting material III and an acid acceptor, simultaneously or successively. Alternatively, the starting material III can be initially introduced into one of the above diluents, after which the starting material II and an acid acceptor are added, simultaneously or in optional sequence, through two separate lines.

In many cases, the reaction is complete immediately after addition of the components; if not, the mixture is stirred further for from 10 minutes to 10 hours at from −50° to 150° C., preferably from 0° to 120° C., in particular from 10° to 50° C.

If an inert gas is used to remove the hydrogen halide, it is advantageous to stir the mixture, after addition of the components, for from 0.2 to 10 hours at from 40° to 100° C.

The end product I is isolated from the reaction mixture in a conventional manner, for example after distilling off the solvent or excess starting materials III, or directly, by filtering off. In the latter case, the residue is washed with water or dilute alkali to remove acidic impurities, and dried. In the case of water-immiscible diluents, the reaction mixture can also be extracted directly with water or with dilute alkali, and then dried and evaporated down. However, it is also possible to dissolve the residue in a water-immiscible solvent, and wash this solution as described. The desired end products are thereby obtained in a pure form; where appropriate, they can be purified by recrystallization, chromatography or distillation.

The starting compounds of the formula II are obtained by a method wherein a compound of the formula

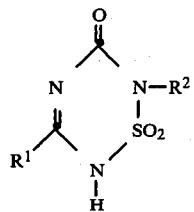

(IV)

where $R^1$ and $R^2$ have the meanings given in claim 1, with the proviso that $R^1$ is not $R^4$—X—, or its alkali metal salt or alkaline earth metal salt, is reacted with an acid halide of phosphoric acid, phosphorous acid, carbonic acid, oxalic acid or sulfurous acid, in the presence or absence of a solvent or diluent and in the presence or absence of a reaction accelerator.

Advantageously, the reaction is carried out in a solvent or diluent which is inert under the reaction conditions, for example halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, o-, m- and p-dichlorobenzene, o-, m- and p-dibromobenzene, o-, m- and p-chlorotoluene or 1,2,4-trichlorobenzene; ethers, eg. ethyl propyl ether, methyl tert.-butyl ether, di-n-butyl ether, diisopropyl ether, anisole, dioxane or ethylene glycol dimethyl ether; nitrohydrocarbons, eg. nitrobenzene, o-, m- and p-chloronitrobenzene or o-nitrotoluene; nitriles, eg. acetonitrile, butyronitrile, isobutyronitrile, benzonitrile or m-chlorobenzonitrile; aliphatic or cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane or 2,2,3-trimethylpentane; esters, eg. ethyl acetate, and mixtures of the above. Other suitable solvents are inorganic acid chlorides, eg. phosphorus oxychloride, or mixtures of these with inert chlorohydrocarbons, such as 1,2-dichloroethane. Advantageously, the solvent is used in an amount of from 100 to 2,000% by weight, preferably from 200 to 700% by weight, based on the starting material of the formula IV.

Preferred acid halides are thionyl chloride, sulfur tetrachloride, phosgene, oxalyl chloride, phosphorus tribromide and in particular phosphorus pentachloride, phosphorus trichloride and phosphorus oxychloride. The reaction is carried out using in general from 1.0 to 1.5, preferably from 1.05 to 1.2, moles of acid halide per mole of starting material IV; where pentavalent phosphorus halide compounds are used, from 0.7 to 1.5, preferably from 1.0 to 1.2, moles of these are used per mole of starting material IV.

Where a phosphorus(V) halide is used as the halogenating agent, it is advisable to use a phosphorus oxyhalide as a diluent; advantageously, this is used in an amount of from 1 to 10 moles per mole of starting material IV.

In this procedure, the phosphorus(V) halide may also be prepared in situ by reacting, for example, a phosphorus(III) halide in a phosphorus oxyhalide or in one of the above inert solvents with the required stoichiometric amount of active halogen, for example according to the method described in U.S. Pat. No. 1,906,440, adding the starting material IV and then carrying out the reaction.

Advantageously, a cyclic or non-cyclic carboxylic acid amide which is disubstituted at the nitrogen atom, a urea which is tetra-substituted by alkyl, or a tertiary amine may be employed as the reaction accelerator, in an amount of from 1 to 10% by weight, based on the starting material IV. Mixtures of the above catalysts are also suitable for the reaction. In addition, salts of diamines, eg. the hydrochlorides of the amines, or a quaternary salt of an amine can also be used. Preferred catalysts are triethylamine, pyridine, N,N-dimethylaniline, N-ethylpiperidine, N-methylpyrrolidine, $\alpha,\beta$- or $\gamma$-picoline, quinoline, isoquinoline, quinazoline, quinoxaline, N-propyldiisopropylamine, 2,6- and 2,4-lutidine, N-(pyrid-4-yl)-pyridinium chloride hydrochloride, p-dimethylaminopyridine, pyrimidine, acridine, dimethylformamide, diethylformamide, formic acid N-methylanilide, N,N-dimethylacetamide, N-methylpyrrolidone and tetramethylurea.

Some of the 6H-1,2,4,6-thiatriazin-5-one-1,1-dioxides required as starting materials of the formula IV are known; both these and the unknown compounds can be prepared by reacting an N-carboalkoxyamidine with an aminosulfonyl halide.

For example, 6-ethyl-3-methyl-5-chloro-6H-1,2,4,6-thiatriazine-1,1-dioxide is obtained when 225 parts of 6-ethyl-3-methyl-6H-1,2,3,6-thiatriazin-5-one-1,1-dioxide is added to a mixture of 1,300 parts of phosphorous oxychloride and 292 parts of phosphorous pentachloride in the course of 2 minutes, while stirring, and the reaction mixture is stirred under reflux for 7 hours and then evaporated down under reduced pressure. The oil which remains is taken up in 350 parts of 1,2-dichloroethane, and the solution is chromatographed over neutral aluminum oxide (activity I) and then evaporated down to give 230 parts (yield: 93% of theory) of 5-chloro-6-ethyl-3-methyl-6H-1,2,4,6-thiatriazine-1,1-dioxide of melting point 57°–59° C. NMR (60 MHz, CDCl$_3$): CH$_3$—C 2.6$\delta$, N—CH$_2$ 3.68–4.03 $\delta$(q), CH$_3$—C 1.2–1.43 $\delta$(t).

EXAMPLE 1

3,6-Dimethyl-5-[(2'-propylidene)-aminoxy]-6H-1,2,4,6-thiatriazine-1,1-dioxide (compound No.1)

212 parts of 3,6-dimethyl-6H-1,2,4,6-thiatriazin-5-one-1,1-dioxide were introduced into a stirred mixture of 292 parts of phosphorus pentachloride and 1,400 parts of phosphorus oxychloride at room temperature, and the mixture was heated to 110° C. in the course of 30 minutes. The reaction mixture was stirred under reflux for 6 hours and then evaporated down under reduced pressure to give 234 parts (yield: 100% of theory) of 5-chloro-3,6-dimethyl-6H-1,2,4,6-thiatriazine-1,1-dioxide of melting point 86°–90° C. NMR (60 MHz, CDCl$_3$): CH$_3$—C 2.4$\delta$, CH$_3$—N 3.68).

13.1 parts of acetone-oxime in 30 parts of methylene chloride and 23 parts of N,N-dimethylcyclohexylamine in 20 parts of methylene chloride were introduced in the course of 10 minutes, via 2 lines, into a stirred solution of 29.3 parts of 5-chloro-3,6-dimethyl-6H-1,2,4,6-thiatriazine-1,1-dioxide in 200 parts of methylene chloride at from 5° to 10° C. Stirring was continued for one hour at room temperature, after which the reaction solution was washed successively with 1N hydrochloric acid and with 10% strength sodium carbonate solution, dried over magnesium sulfate and chromatographed over silica gel. After evaporating down under reduced pressure, 22 parts (63% of theory) of 3,6-dimethyl-5-[(2'-propylidene)-aminoxy]-6H-1,2,4,6-thiatriazine-1,1-dioxide of melting point 115°–118° C. were obtained.

EXAMPLE 2

6-Methyl-3-methoxy-5-(2-phenylethoxy)-6H-1,2,4,6-thiatriazine-1,1-dioxide (compound No.2)

22 parts of 2-phenylethanol and 26.8 parts of tri-n-propylamine were added, in the course of 10 minutes, to 31.7 parts of 5-chloro-6-methyl-3-methoxy-6H-1,2,4,6-thiatriazine-1,1-dioxide in 200 parts of 1,2-dichloroethane at from 0° to 5° C., while stirring. Stirring was continued for 15 minutes at room temperature, after which the reaction solution was washed successively with 1N hydrochloric acid, with 0.5N sodium hydroxide solution and with water, dried over magnesium sulfate and chromatographed over neutral aluminum oxide. After evaporating down under reduced pressure, 36 parts (81% of theory) of 6-methyl-3-methoxy-5-(2-phenylethoxy)-6H-1,2,4,6-thiatriazine-1,1-dioxide of melting point 74°–77° C. were obtained.

EXAMPLE 3

6-Methyl-3-methoxy-5-dimethylphosphono-6H-1,2,4,6-thiatriazine-1,1-dioxide (compound No.3)

145 parts of trimethyl phosphite were added, in the course of 40 minutes, to 165 parts of 5-chloro-6-methyl-3-methoxy-6H-1,2,4,6-thiatriazine-1,1-dioxide in 550 parts of toluene at from 38° to 41° C., while stirring. The reaction mixture was heated to 70° C. in the course of 30 minutes, and stirring was continued at this temperature for 1¾ hours. Thereafter, the solution was decanted off from the small amount of tacky residue, and was freed from volatile constituents at 80° C./0.2 mbar. The residue was dissolved in 300 parts of ethyl acetate, and the solution was chromatographed over neutral aluminum oxide. After evaporating down under reduced pressure, 192 parts (96% of theory) of 6-methyl-3-methoxy-5-dimethylphosphono-6H-1,2,4,6-thiatriazine-1,1-dioxide of $n_D^{25} = 1.4998$ were obtained.

EXAMPLE 4

6-Methyl-3-methoxy-5-(4-phenyl-n-butoxy)-6H-1,2,4,6-thiatriazine-1,1-dioxide (compound No.4)

A mixture of 27 parts of 4-phenyl-n-butanol with 23 parts of N,N-dimethylcyclohexylamine, and 31.7 parts of 5-chloro-6-methyl-3-methoxy-6H-1,2,4,6-thiatriazine-1,1-dioxide, were added side by side, in the course of 15 minutes, to 250 parts of methylene chloride at from 10° to 15° C., while stirring. Stirring was continued for one hour at room temperature, after which the reaction mixture was washed with 1N hydrochloric acid and with 10% strength sodium carbonate solution, and dried over magnesium sulfate. After evaporating down under reduced pressure, 40 parts of the 6-methyl-3-methoxy-5-(4-phenylbutoxy)-6H-1,2,4,6-thiatriazine-1,1-dioxide of melting point 74°–78° C. were obtained.

The following 1,2,4,6-thiatriazine-1,1-dioxides of the formula I were, or may be, obtained in a similar manner:

| Compound no. | R¹ | Y | R² | R³ | M.p. [°C.]/$n_D^{25}$ |
|---|---|---|---|---|---|
| 5 | H | O | CH₂CN | H | |
| 6 | H | O | CH₂CN | CH₃ | |
| 7 | CH₃ | S | CH₂CN | H | |
| 8 | CH₃ | O | CH₂CN | CH₃ | |
| 9 | CH₃ | O | CH₂CN | C₂H₅ | |
| 10 | CH₃ | O | CH₂—CH₂—CN | H | |
| 11 | H | O | CH₂—CH₂—CN | H | |
| 12 | CH₃ | O | CH₂—CH₂—CN | CH₃ | 1.5040 |
| 13 | H | O | CH₂—CH₂—CN | CH₃ | |
| 14 | CH₃ | S | CH₂—CH₂—CN | CH₃ | |
| 15 | C₂H₅ | O | CH₂—CH₂—CN | CH₃ | |
| 16 | (CH₃)₂N | O | CH₂—CH₂—CN | CH₃ | |
| 17 | CH₃ | O | (CH₂)₃—CN | CH₃ | |
| 18 | CH₃ | O | (CH₂)₄—CN | CH₃ | |
| 19 | CH₃ | O | CH₂—CH=CH—CN | CH₃ | |
| 20 | CH₃ | O | CH₂—C≡C—CN | CH₃ | |
| 21 | CH₃ | O | CH₂—CH₂—SCN | i-C₃H₇ | |
| 22 | CH₃ | O | (CH₂)₃SCN | CH₃ | |
| 23 | CH₃ | O | CH₂—CH₂—NO₂ | CH₃ | |
| 24 | CH₃ | O | (CH₂)₃NO₂ | CH₃ | |
| 25 | CH₃ | O | CH₂—CH₂—O—CH₂—CH=CH₂ | H | |
| 26 | (CH₃)₂N | O | CH₂—CH₂—O—CH₂—CH=CH₂ | CH₃ | |
| 27 | CH₃ | O | CH₂—CH₂—O—CH₂—CH=CH₂ | CH₃ | |
| 28 | CH₃ | O | CH₂—CH₂—O—CH₂—C≡CH | CH₃ | |
| 29 | CH₃ | O | CH₂—CH₂—S—CH₂—CH=CH₂ | CH₃ | |
| 30 | CH₃ | O | CH₂—CH=CH—CH₂—O—CH₂—CH=CH₂ | CH₃ | |
| 31 | CH₃ | O | (CH₂)₂—O—(CH₂)₂—O—CH₃ | CH₃ | 1.4860 |
| 32 | CH₃ | S | (CH₂)₂—O—(CH₂)₂—S—CH₃ | CH₃ | |
| 33 | CH₃ | O | CH₂—CH₂—C(=O)—CH=CH₂ | CH₃ | |
| 34 | CH₃ | O | CH₂—CH=CH—CO₂CH₃ | CH₃ | |
| 35 | CH₃ | O | CH₂—C≡C—CO₂CH₃ | CH₃ | |
| 36 | CH₃ | O | N=C(CH₃)₂ | CH₃ | 112–117 |
| 37 | C₂H₅ | O | 2-(4-chlorophenyl)-ethyl | i-C₃H₇ | |
| 38 | CH₃ | O | 2-(3-chlorophenyl)-ethyl | CH₃ | 1.5449 |
| 39 | CH₃ | O | 2-phenyl-ethyl | CH₃ | |
| 40 | (CH₃)₂N | O | 2-(2-chlorophenyl)-ethyl | CH₃ | |
| 41 | CH₃ | O | 2-(3-chlorophenyl)-ethyl | CH₃ | |
| 42 | CH₃ | O | 2-(3-methylphenyl)-ethyl | CH₃ | |
| 43 | CH₃ | O | 2-(3-trifluorethylphenyl)-ethyl | H | |
| 44 | CH₃ | O | 2-(3-cyanophenyl)-ethyl | CH₃ | |
| 45 | CH₃ | O | 2-(3-methoxyphenyl)-ethyl | CH₃ | |
| 46 | CH₃ | O | 3-phenyl-n-propyl | CH₃ | |
| 47 | CH₃ | O | 2-(2,4-dichlorophenyl)-ethyl | CH₃ | |
| 48 | CH₃ | O | 2-(2,4,6-trichlorophenyl)-ethyl | CH₃ | |
| 49 | CH₃ | O | 4-phenyl-n-butyl | CH₃ | |
| 50 | H | O | 2-phenyl-ethyl | CH₃ | |
| 51 | CH₃ | O | 2-(3-chloro-4-methoxyphenyl)-ethyl | CH₃ | |
| 52 | CH₃ | O | 2-(2-chloro-4-CF₃-phenyl)-ethyl | CH₃ | |
| 53 | (CH₃)₂N | O | styrene | CH₃ | |
| 54 | CH₃ | O | 2-(3-chlorophenyl)-vinyl | CH₃ | |
| 55 | CH₃ | O | 3-phenyl-prop-2-enyl | CH₃ | |
| 56 | CH₃ | O | 3-phenyl-prop-2-enyl | H | |
| 57 | CH₃ | O | PO(OCH₃)₂ | CH₃ | |
| 58 | CH₃ | O | PO(OC₂H₅)₂ | CH₃ | |
| 59 | CH₃ | O | PO(OCH₃)(OC₂H₅) | CH₃ | |
| 60 | CH₃ | S | 2-phenyl-ethyl | CH₃ | |
| 61 | CH₃ | O | 2-(4-chloro-3-methoxy-phenyl)-ethyl | CH₃ | |
| 62 | (CH₃)₂N | O | 2-phenylethyl | C₂H₅ | |
| 63 | C₂H₅ | O | CH₂—CH₂—O—CH₂—CH=CH₂ | CH₃ | |
| 64 | i-C₃H₇ | O | CH₂—CH₂—O—CH₂—CH=CH₂ | CH₃ | |
| 65 | n-C₃H₇ | S | CH₂—CH₂—O—CH₂—CH=CH₂ | CH₃ | |
| 66 | (CH₃)₂N | O | CH₂—CH₂—O—CH₂—C≡CH | CH₃ | |
| 67 | C₂H₅ | O | CH₂—CH₂—S—CH₂—CH=CH₂ | CH₃ | |
| 68 | C₂H₅ | O | (CH₃)₂—O—(CH₂)₂—OCH₃ | CH₃ | |
| 69 | nC₄H₉ | O | (CH₂)₂—O—(CH₂)₂—O—CH₃ | CH₃ | |
| 70 | C₂H₅ | O | (CH₂)₂O—(CH₂)₂—S—CH₃ | CH₃ | |
| 71 | C₂H₅ | O | N=C(CH₃)₂ | C₂H₅ | |
| 72 | CH₃ | O | N=C(CH₃)₂ | C₂H₅ | 1.5328 |
| 73 | CH₃ | O | 2-phenylethyl | C₂H₅ | |
| 74 | CH₃ | O | 2-(3-chlorophenyl)-ethyl | C₂H₅ | |
| 75 | CH₃ | O | 2-(3-trifluoromethylphenyl)- | C₂H₅ | |

-continued

| | | | | | |
|---|---|---|---|---|---|
| 76 | CH$_3$ | O | 2-(3-methoxyphenyl)-ethyl | i-C$_3$H$_7$ | |
| 77 | CH$_3$ | O | 2-(2,4-dichlorophenyl)-ethyl | C$_2$H$_5$ | |
| 78 | CH$_3$ | O | PO(OCH$_3$)$_2$ | C$_2$H$_5$ | |
| 79 | (CH$_3$)$_2$N | O | 2-(4-cyanophenyl)-ethyl | C$_2$H$_5$ | |
| 80 | C$_2$H$_5$ | O | 2-phenylethyl | CH$_2$—CH$_2$—Cl | |
| 81 | CH$_3$ | O | CH$_2$—CH$_2$—CN | CH$_2$—CH$_2$—Cl | |

| Compound no. | R$^4$ (R$^1$=R$^4$—X—) | X | Y | R$^2$ | R$^3$ | M.p. [°C.]/n$_D^{25}$ |
|---|---|---|---|---|---|---|
| 82 | CH$_3$ | O | O | CH$_2$CN | H | |
| 83 | CH$_3$ | S | O | CH$_2$CN | CH$_3$ | |
| 84 | CH$_3$ | O | S | CH$_2$CN | H | |
| 85 | CH$_3$ | O | O | CH$_2$CN | CH$_3$ | |
| 86 | CH$_3$ | O | O | CH$_2$CN | C$_2$H$_5$ | |
| 87 | CH$_3$ | O | O | CH$_2$—CH$_2$—CN | H | |
| 88 | CH$_3$ | O | O | CH$_2$—CH$_2$—CN | CH$_3$ | 162–165 |
| 89 | CH$_3$ | O | S | CH$_2$—CH$_2$—CN | CH$_3$ | 129–132 |
| 90 | CH$_3$ | O | O | (CH$_2$)$_3$—CN | H | |
| 91 | CH$_3$ | O | O | (CH$_2$)$_3$—CN | CH$_3$ | |
| 92 | CH$_3$ | O | O | (CH$_2$)$_3$—CN | CH$_4$ | |
| 93 | CH$_3$ | O | O | CH$_2$—CH$_2$—CN | i-C$_3$H$_7$ | |
| 94 | CH$_3$ | O | O | (CH$_2$)$_3$—CN | CH$_3$ | |
| 95 | CH$_3$ | O | O | (CH$_2$)$_4$—CN | CH$_3$ | |
| 96 | CH$_3$ | O | O | CH$_2$—CH=CH—CN | CH$_3$ | |
| 97 | CH$_3$ | O | O | CH$_2$—C≡C—CN | CH$_3$ | |
| 98 | CH$_3$ | O | O | CH$_2$—CH$_2$—SCN | CH$_3$ | |
| 99 | CH$_3$ | O | O | (CH$_2$)$_3$SCN | CH$_3$ | |
| 100 | CH$_3$ | O | O | CH$_2$—CH$_2$—NO$_2$ | CH$_3$ | |
| 101 | CH$_3$ | O | O | (CH$_2$)$_3$NO$_2$ | CH$_3$ | |

| Compound no. | R$^4$ | X | Y | R$^2$ | R$^3$ | M.p. [°C.]/n$_D^{25}$ |
|---|---|---|---|---|---|---|
| 102 | CH$_3$ | O | O | CH$_2$—CH$_2$—O—CH$_2$—CH=CH$_2$ | H | |
| 103 | CH$_3$ | S | O | CH$_2$—CH$_2$—O—CH$_2$—CH=CH$_2$ | | |
| 104 | CH$_3$ | O | O | CH$_2$—CH$_2$—O—CH$_2$—CH=CH$_2$ | CH$_3$ | 1.5049 |
| 105 | CH$_3$ | O | O | CH$_2$—CH$_2$—O—CH$_2$—C≡CH | CH$_3$ | 1.5009 |
| 106 | CH$_3$ | O | O | CH$_2$—CH$_2$—S—CH$_2$—CH=CH$_2$ | CH$_3$ | |
| 107 | CH$_3$ | O | O | CH$_2$—CH=CH—CH$_2$—O—CH$_2$—CH=CH$_2$ | CH$_3$ | |
| 108 | CH$_3$ | O | O | (CH$_2$)$_2$—O—(CH$_2$)$_2$—O—CH$_3$ | CH$_3$ | 36–39 |
| 109 | CH$_3$ | O | S | (CH$_2$)$_2$—O—(CH$_2$)$_2$—S—CH$_3$ | CH$_3$ | |
| 110 | CH$_3$ | O | O | CH$_2$—CH$_2$—C(=O)—CH=CH$_2$ | CH$_3$ | |
| 111 | CH$_3$ | O | O | CH$_2$—CH=CH—CO$_2$CH$_3$ | CH$_3$ | |
| 112 | CH$_3$ | O | O | CH$_2$—C≡C—CO$_2$CH$_3$ | CH$_3$ | |
| 113 | CH$_3$ | O | O | N=C(CH$_3$)$_2$ | CH$_2$—CH$_2$—Cl | |
| 114 | C$_2$H$_5$ | O | O | 2-(4-chlorophenyl)-ethyl | CH$_3$ | |
| 115 | CH$_3$ | O | O | 2-(3-chlorophenyl)-ethyl | CH$_3$ | |
| 116 | CH$_3$ | O | O | 2-phenylethyl | i-C$_3$H$_7$ | |
| 117 | CH$_3$ | O | O | 2-(2-chlorophenyl)-ethyl | CH$_3$ | |
| 118 | CH$_3$ | O | O | 2-(3-chlorophenyl)-ethyl | CH$_3$ | 93–95 |
| 119 | CH$_3$ | O | O | 2-(3-methylphenyl)-ethyl | CH$_3$ | |
| 120 | CH$_3$ | S | O | 2-(3-trifluoromethylphenyl)-ethyl | H | |
| 121 | CH$_3$ | O | O | 2-(3-cyanophenyl)-ethyl | CH$_3$ | |
| 122 | CH$_3$ | O | O | 2-(3-methoxyphenyl)-ethyl | CH$_3$ | |
| 123 | CH$_3$ | O | O | 3-phenyl-n-propyl | CH$_3$ | 1.5430 |
| 124 | CH$_3$ | O | O | 2-(3,4-dichlorophenyl)-ethyl | CH$_3$ | |
| 125 | CH$_3$ | O | O | 2-(2,4,6-trichlorophenyl)-ethyl | CH$_3$ | |
| 126 | CH$_3$ | S | O | 4-phenyl-n-butyl | CH$_3$ | |
| 127 | CH$_3$ | O | O | 2-phenyl-ethyl | H | |
| 128 | CH$_3$ | O | O | 2-(3-chloro-4-methoxyphenyl)-ethyl | CH$_3$ | |
| 129 | CH$_3$ | O | O | 2-(2-chloro-4-trifluoromethylphenyl)-ethyl | CH$_3$ | |
| 130 | CH$_3$ | O | O | styryl | CH$_3$ | |
| 131 | CH$_3$ | O | O | 2-(3-chlorophenyl)-vinyl | CH$_3$ | |
| 132 | CH$_3$ | O | O | 3-phenyl-prop-2-enyl | CH$_3$ | |
| 133 | CH$_3$ | O | O | 3-phenyl-prop-2-enyl | H | 84–86 |
| 134 | CH$_3$ | O | | PO(OC$_2$H$_5$)$_2$ | CH$_3$ | |
| 135 | CH$_3$ | O | | PO(OCH$_3$)$_2$ | H | |
| 136 | CH$_3$ | S | | PO(OCH$_3$)(OC$_2$H$_5$) | CH$_3$ | |
| 137 | CH$_3$ | O | S | 2-phenyl-ethyl | CH$_3$ | |
| 138 | CH$_3$ | O | O | 2-(4-chloro-3-methoxyphenyl)-ethyl | CH$_3$ | |
| 139 | CH$_3$ | S | O | 2-phenyl-ethyl | CH$_3$ | |
| 140 | C$_2$H$_5$ | O | O | CH$_2$CH$_2$—O—CH$_2$—CH=CH$_2$ | CH$_3$ | |
| 141 | i-C$_3$H$_7$ | O | O | CH$_2$—CH$_2$—O—CH$_2$—CH=CH$_2$ | CH$_3$ | |

-continued

| | | | | | | |
|---|---|---|---|---|---|---|
| 142 | n-C$_3$H$_7$ | O | S | CH$_2$—CH$_2$—O—CH$_2$—CH=CH$_2$ | CH$_3$ | |
| 143 | CH$_3$ | O | O | CH$_2$—CH$_2$—O—CH$_2$—C≡CH | C$_2$H$_5$ | |
| 144 | C$_2$H$_5$ | O | O | CH$_2$—CH$_2$—S—CH$_2$—CH=CH$_2$ | CH$_3$ | |
| 145 | C$_2$H$_5$ | O | O | (CH$_2$)$_2$—O—(CH$_2$)$_2$—OCH$_3$ | CH$_3$ | |
| 146 | n-C$_4$H$_9$ | O | O | (CH$_2$)$_2$—O—(CH$_2$)$_2$—O—CH$_3$ | CH$_3$ | |
| 147 | C$_2$H$_5$ | O | O | (CH$_2$)$_2$—O—(CH$_2$)$_2$—S—CH$_3$ | CH$_3$ | |
| 148 | CH$_3$ | O | O | N=C(CH$_3$)$_2$ | CH$_3$ | 132–135 |
| 149 | CH$_3$ | S | O | N=C(CH$_3$)$_2$ | C$_2$H$_5$ | |
| 150 | CH$_3$ | O | O | 2-phenylethyl | C$_2$H$_5$ | |
| 151 | CH$_3$ | O | O | 2-(3-chlorophenyl)-ethyl | C$_2$H$_5$ | |
| 152 | CH$_3$ | S | O | 2-(3-trifluoromethylphenyl)-ethyl | C$_2$H$_5$ | |
| 153 | CH$_3$ | O | O | 2-(3-methoxyphenyl)-ethyl | i-C$_3$H$_7$ | |
| 154 | CH$_3$ | O | O | 2-(2,4-dichlorophenyl)-ethyl | C$_2$H$_5$ | |
| 155 | CH$_3$ | O | | PO(OCH$_3$)$_2$ | C$_2$H$_5$ | |
| 156 | CH$_3$ | O | S | 2-(4-cyanophenyl)-ethyl | C$_2$H$_5$ | |
| 157 | C$_2$H$_5$ | O | O | 2-phenylethyl | CH$_2$—CH$_2$—Cl | |
| 158 | CH$_3$ | O | O | 2-cyanoethyl | CH$_2$—CH$_2$—Cl | |
| 159 | CH$_3$ | O | O | CH$_2$—CH[CN]CH$_3$ | CH$_3$ | |
| 160 | CH$_3$ | O | O | (CH$_2$)$_4$SCN | CH$_3$ | |
| 161 | CH$_3$ | O | O | (CH$_2$)$_2$—O(CH$_2$)$_2$—allyl | CH$_3$ | |
| 162 | CH$_3$ | O | O | CH$_2$CH≡CH—CO$_2$C$_2$H$_5$ | CH$_3$ | |
| 163 | C$_2$H$_5$ | O | S | CH$_2$—C≡C—CO$_2$C$_2$H$_5$ | CH$_3$ | |
| 164 | CH$_3$ | O | O | N=C(CH$_3$)C$_2$H$_5$ | CH$_3$ | |
| 165 | CH$_3$ | O | O | N=CH—CH$_3$ | CH$_3$ | |
| 166 | CH$_3$ | O | O | N=CH—C$_2$H$_5$ | CH$_3$ | |
| 167 | CH$_3$ | O | O | 2-(4-chlorophenyl)-ethyl | CH$_3$ | 117–121 |
| 168 | CH$_3$ | O | O | 2-(3,4-dichlorophenyl)-ethyl | CH$_3$ | |
| 169 | CH$_3$ | O | O | 2-(4-cyanophenyl)-ethyl | CH$_3$ | |
| 170 | CH$_3$ | S | O | 2-(3-trifluoromethoxyphenyl)-ethyl | CH$_3$ | |
| 171 | CH$_3$ | O | O | 2-nitrobenzyl | CH$_3$ | 171–173 |
| 172 | CH$_3$ | O | O | 2-chloro-4-nitrobenzyl | CH$_3$ | |
| 173 | CH$_3$ | O | S | 4-nitrobenzyl | CH$_3$ | |
| 174 | CH$_3$ | O | O | 4-nitrobenzyl | CH$_3$ | 187–190 |
| 175 | CH$_3$ | O | O | 3-nitrobenzyl | CH$_3$ | 171–174 |
| 176 | CH$_3$ | O | O | 2-chloro-6-nitrobenzyl | CH$_3$ | 163–166 |
| 177 | CH$_3$ | O | O | 2-(2-nitrophenoxy)-ethyl | CH$_3$ | |
| 178 | CH$_3$ | O | O | 2-(3-nitrophenoxy)-ethyl | CH$_3$ | |
| 179 | CH$_3$ | O | O | 2-(4-cyanophenoxy)-ethyl | CH$_3$ | |
| 180 | CH$_3$ | O | S | 2-(3-trifluorophenoxy)-ethyl | CH$_3$ | |
| 181 | CH$_3$ | O | O | 2-(3-trifluoromethoxy-phenoxy)-ethyl | CH$_3$ | |
| 182 | CH$_3$ | O | O | 2-(4-chlorophenoxy)-ethyl | CH$_3$ | 136–138 |
| 183 | CH$_3$ | O | O | 2-(3-chlorophenoxy)-ethyl | CH$_3$ | 88–90 |
| 184 | CH$_3$ | O | O | 2-(2-chlorophenoxy)-ethyl | CH$_3$ | |
| 185 | CH$_3$ | O | O | 2-(3,5-dichlorophenoxy)-ethyl | CH$_3$ | |
| 186 | CH$_3$ | O | O | 2-(2,4-dichlorophenoxy)-ethyl | CH$_3$ | 127–129 |
| 187 | CH$_3$ | O | O | 2-(2,4,6-trichlorophenoxy)-ethyl | CH$_3$ | |
| 188 | CH$_3$ | O | O | 2-(2-chloro-4-methylphenoxy)-ethyl | CH$_3$ | |
| 189 | CH$_3$ | O | O | 2-(2,4-dimethyl-phenoxy)-ethyl | CH$_3$ | |
| 190 | CH$_3$ | O | O | 2-(2-chloro-4-trifluormethyl-phenoxy)-ethyl | CH$_3$ | |
| 191 | CH$_3$ | O | O | 2-(3-methoxy-phenoxy)-ethyl | CH$_3$ | |
| 192 | CH$_3$ | O | O | 2-phenoxy-vinyl | CH$_3$ | |
| 193 | CH$_3$ | O | O | 3-phenoxy-prop-1-enyl | CH$_3$ | |
| 194 | CH$_3$ | S | O | 2-(4-chlorophenoxy)-ethyl | CH$_3$ | |
| 195 | CH$_3$ | O | O | 4-phenoxy-n-but-2-inyl | CH$_3$ | 98–101 |
| 196 | CH$_3$ | O | O | 4-(4-chlorophenoxy)-n-but-2-ynyl | CH$_3$ | |
| 197 | CH$_3$ | O | O | 4-(2,4-dichlorophenoxy)-n-but-2-ynyl | CH$_3$ | |
| 198 | CH$_3$ | O | O | 4-(3-chlorophenoxy)-n-but-2-ynyl | CH$_3$ | |
| 199 | CH$_3$ | O | O | 4-(4-fluorophenoxy)-n-but-2-ynyl | CH$_3$ | 102–104 |
| 200 | CH$_3$ | O | O | 4-(2,4-dichlorophenoxy)-n-but-2-ynyl | CH$_3$ | |
| 201 | CH$_3$ | O | O | 4-(2-methyl-4-chlorophenoxy)-n-but-2-inyl | CH$_3$ | |
| 202 | CH$_3$ | O | O | CH(CH=CH$_2$)—CO$_2$C$_2$H$_5$ | CH$_3$ | 1.5018 |
| 203 | CH$_3$ | O | O | 2-phenoxy-ethyl | CH$_3$ | 81–84 |
| 204 | CH$_3$ | O | O | 2-(2-methylphenyl)-ethyl | CH$_3$ | 102–104 |
| 205 | CH$_3$ | O | O | 2-phenyl-n-propyl | CH$_3$ | 67–68 |
| 206 | CH$_3$ | O | O | 3-(2,4-dichlorophenoxy)-n-propyl | CH$_3$ | 96–98 |
| 207 | CH$_3$ | O | O | 3-(4-chlorophenoxy)-n-propyl | CH$_3$ | 120–123 |
| 208 | CH$_3$ | O | O | 3-(3-trifluoromethylphenoxy)-n-propyl | CH$_3$ | 70–73 |

-continued

| | | | | | | |
|---|---|---|---|---|---|---|
| 209 | CH₃ | O | O | 3-(4-chlorophenyl)-n-propyl | CH₃ | |
| 210 | CH₃ | O | O | 3-(2,4-dichlorophenyl)-n-propyl | CH₃ | |
| 211 | CH₃ | O | O | 3-(3-chlorophenoxy)-n-propyl | CH₃ | 125–128 |
| 212 | CH₃ | O | S | 2-(3-chlorophenyl)-ethyl | CH₃ | 67–69 |
| 213 | CH₃ | O | O | 3-(p-tolyl)-n-propyl | CH₃ | |
| 214 | CH₃ | O | O | 2-(2-chlorophenyl)-ethyl | CH₃ | 116–119 |
| 215 | CH₃ | O | O | 2-(4-methyl-2-methoxy-phenoxy)-ethyl | CH₃ | 96–99 |
| 216 | C₂H₅ | O | O | (CH₂)₂—O—(CH₂)₂—O—CH₃ | C₂H₅ | 1.4879 |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 175 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 174 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 183 is well mixed with 3 parts by weight of the sodium salt of diisobutylnaphthalene-alpha-sulfonic acid, 17 parts by weight of the sodium-salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 182 is intimately mixed with 97 parts by weight of particulate kaolin. A dust is obtained containing 3% by weight of the active ingredient.

VII. 30 parts by weight of compound no. 176 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 171 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or formulations containing them, may be applied pre- or postemergence. The agents may be applied to the location before the unwanted plants have germinated from seed or sprouted from vegetative plant parts, or they may be applied to the leaves of unwanted and crop plants. Preferably, the novel active ingredients are applied during or after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants germinating and growing beneath the crop plants (post-directed, lay-by treatment).

The amount of active ingredient applied depends on the time of the year and the growth stage of the plants, and varies from 0.1 to 10 kg/ha and more, but is preferably from 0.5 to 4 kg/ha. The higher application rates are particularly suitable for total elimination of vegetation.

The herbicidal action of compounds of the formula I is demonstrated in greenhouse experiments.

The vessels employed were plastic flowerpots having a volume of 300 cm$^3$, and which were filled with a sandy loam containing about 1.5% humus. In the case of soybeans and rice, peat was added to ensure good growth. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. Application rates varied from compound to compound, and were either 0.5, 1.0, 2.0 or 4.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated.

The pots were set up in the greenhouse—species from warmer areas at from 20° to 30° C. and species from moderate climates at 15° to 25° C. The experiments were run for from 3 to 5 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants were *Datura stramonium, Galium aparine, Oryza sativa, Sinapis alba, Solanum nigrum, Gossypium hirsutum, Glycine max.*, and *Triticum aestivum*.

The greenhouse experiments reveal that the novel compounds are suitable, both or pre- and postemergence application, for combating unwanted plants. Their use as selective herbicidal agents in crops is of particular interest.

On preemergence application, compounds nos. 171, 174, 175, 176, 182 and 183 combated the unwanted plants used in the experiments, and caused little or no damage to the crop plants. Further, compounds nos. 176 and 183, applied postemergence at a rate of 2.0 kg/ha, had a good action on unwanted plants.

The agents may be applied when both crop plants and unwanted plants are in the pre- or postemergence stage at the same time. However, the agents may also be applied when the crop plants are already established, but the weeds and weedy grasses have not emerged or are in the process of emerging.

The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |

| Botanical name | Common name |
| --- | --- |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture componentes are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A 1,2,4,6-thiatriazine-1,1-dioxide of the formula

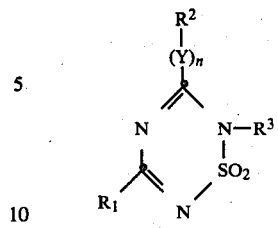

where $R^1$ is hydrogen or a saturated or unsaturated, straight-chain or branched aliphatic radical of no more than 10 carbon atoms, or is a saturated, straight-chain or branched aliphatic radical of no more than 10 carbon atoms which is substituted by halogen, alkoxy or alkylmercapto of 1 to 4 carbon atoms, or is an alkylamino or dialkylamino radical where alkyl is of 1 to 6 carbon atoms, cycloalkyl of 3 to 7 carbon atoms, or phenyl which is unsubstituted or substituted by halogen, alkyl or alkoxy of 1 to 4 carbon atoms, or is unsubstituted or halogen-substituted benzyl, or is $R^4$—X—, where $R^4$ has the meanings given for $R^1$, except alkylamino and dialkylamino, and X is oxygen, sulfur, —SO— or —SO$_2$—, $R^2$ is a saturated or unsaturated, straight-chain or branched aliphatic radical of no more than 10 carbon atoms which is substituted by cyano, alkenyloxy, alkynyloxy, each of no more than 4 carbon atoms, or is an alkyleneglycolalkyl radical of no more than 6 carbon atoms which is substituted by alkyl, alkenyl or alkynyl, each of no more than 4 carbon atoms, or is an alkenyl or alkynyl radical, each of no more than 4 carbon atoms, which is substituted by alkoxycarbonyl or alkylmercaptocarbonyl of no more than 5 carbon atoms, or is an alkylideneamino or dialkylmethylideneamino radical of no more than 6 carbon atoms, or a phenylalkyl, phenylalkenyl or phenylalkynyl radical of 8 to 12 carbon atoms which is unsubstituted or substituted in the phenyl ring by halogen, alkyl, haloalkyl, alkoxy, haloalkoxy, alkylmercapto or haloalkylmercapto, each of no more than 4 carbon atoms, nitro, cyano or thiocyano, $R^3$ is hydrogen or a saturated or unsaturated, straight-chain or branched aliphatic radical of no more than 10 carbon atoms, or is a saturated, straight-chain or branched aliphatic radical of no more than 10 carbon atoms which is substituted by halogen or alkoxy of 1 to 4 carbon atoms, or is cycloalkyl of 3 to 7 carbon atoms, Y is oxygen, sulfur, —SO— or —SO$_2$— and n is is 1, or where $R^2$ is benzyl which is substituted by nitro or by halogen and nitro, or is a phenoxyalkyl, phenoxyalkenyl or phenoxyalkynyl radical of 8 to 12 carbon atoms which is substituted in the phenyl ring by halogen, alkyl, haloalkyl, alkoxy, haloalkoxy, alkylmercapto or haloalkylmercapto, each of no more than 4 carbon atoms, nitro, cyano or thiocyano, when $R^1$ is $R^4$—X— and n is 1, or where $R^2$ is dialkylphosphono when n is 0.

2. A 1,2,4,6-thiatriazine-1,1-dioxide of the formula I as claimed in claim 1, where $R^1$ is $R^4$—X—, $R^4$ is alkyl of 1 to 4 carbon atoms and X is oxygen, $R^2$ is dialkylphosphono, where alkyl is of 1 to 4 carbon atoms, $R^3$ is alkyl of 1 to 4 carbon atoms, and n is 0.

3. A 1,2,4,6-thiatriazine-1,1-dioxide of the formula I as claimed in claim 1, where $R^1$ is $R^4$—X—, $R^4$ is alkyl of 1 to 4 carbon atoms and X is oxygen or sulfur, $R^2$ is phenoxyalkyl of 7 to 10 carbon atoms which is unsubstituted or substituted in the phenyl ring by halogen, $R^3$ is alkyl of 1 to 4 carbon atoms, and Y is oxygen or sulfur.

4. A 1,2,4,6-thiatriazine-1,1-dioxide of the formula I as claimed in claim 1, where $R^1$ and $R^3$ are alkyl of 1 to 4 carbon atoms, $R^2$ is a cyano-substituted, saturated or unsaturated aliphatic radical of no more than 4 carbon atoms, and Y is oxygen or sulfur.

5. A 1,2,4,6-thiatriazine-1,1-dioxide of the formula I as claimed in claim 1, where $R^1$ is $R^4$—X—, $R^4$ is alkyl of 1 to 4 carbon atoms and X is oxygen or sulfur, $R^2$ is phenylalkyl, phenylalkenyl or phenylalkynyl of 8 to 12 carbon atoms which is unsubstituted or substituted in the phenyl ring by halogen, cyano, nitro or alkyl, $R^3$ is alkyl of 1 to 4 carbon atoms, and Y is oxygen or sulfur.

6. A 1,2,4,6-thiatriazine-1,1-dioxide of the formula I as set forth in claim 1, where $R^1$ is $R^4$—X—, where $R^4$ is alkyl of 1 to 4 carbon atoms and X is oxygen, $R^2$ is benzyl which is substituted by nitro or by halogen and nitro, $R^3$ is alkyl of 1 to 4 carbon atoms and Y is oxygen.

7. 6-Methyl-5-(2-(3-chlorophenyl)-ethoxy)-3-methoxy-6H-1,2,4,6-thiatriazine-1,1-dioxide.

8. A herbicide containing inert additives and a 1,2,4,6-thiatriazine-1,1-dioxide of the formula I as claimed in claim 1.

9. A herbicide containing inert additives and a 1,2,4,6-thiatriazine-1,1-dioxide of the formula I as claimed in claim 2.

10. A herbicide containing inert additives and a 1,2,4,6-thiatriazine-1,1-dioxide of the formula I as claimed in claim 5.

11. A process for combating the growth of unwanted plants, wherein the plants and/or the soil are treated with a herbicidally effective amount of a 2H-1,2,4,6-thiatriazine-1,1-dioxide of the formula I as claimed in claim 1.

* * * * *